(12) United States Patent
Watanabe et al.

(10) Patent No.: US 8,034,737 B2
(45) Date of Patent: Oct. 11, 2011

(54) CATALYST FOR PRODUCING ACRYLONITRILE AND PROCESS FOR PRODUCING ACRYLONITRILE

(75) Inventors: Hirokazu Watanabe, Yokohama (JP); Motoo Yanagita, Yokohama (JP); Kenichi Miyaki, Yokohama (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 286 days.

(21) Appl. No.: 12/393,494

(22) Filed: Feb. 26, 2009

(65) Prior Publication Data
US 2009/0221843 A1 Sep. 3, 2009

(30) Foreign Application Priority Data
Mar. 3, 2008 (JP) .................................. 2008-052272

(51) Int. Cl.
*B01J 21/08* (2006.01)
(52) U.S. Cl. ..................... 502/212; 502/248; 502/249
(58) Field of Classification Search ........................ None
See application file for complete search history.

(56) References Cited

U.S. PATENT DOCUMENTS

| | | | |
|---|---|---|---|
| 3,882,159 A | 5/1975 | Callahan et al. |
| 4,536,483 A | 8/1985 | Sasaki et al. |
| 5,212,137 A | 5/1993 | Suresh et al. |
| 5,688,739 A | 11/1997 | Drenski et al. |
| 5,834,394 A | 11/1998 | Chen et al. |
| 6,084,119 A | 7/2000 | Midorikawa et al. |
| 6,420,307 B1 | 7/2002 | Wu et al. |
| 6,642,405 B1 | 11/2003 | Mori et al. |
| 6,653,496 B1 | 11/2003 | Mori et al. |
| 2004/0106817 A1 | 6/2004 | Paparizos et al. |
| 2004/0248734 A1 | 12/2004 | Miyaki et al. |

FOREIGN PATENT DOCUMENTS

| | | |
|---|---|---|
| DE | 33 11 521 A1 | 1/1984 |
| EP | 1 223 162 A1 | 7/2002 |
| JP | 58-57422 | 12/1983 |
| JP | 59-193136 | 11/1984 |
| JP | 2-56938 | 12/1990 |
| JP | 8-27089 | 1/1996 |
| JP | 10-43595 | 2/1998 |
| JP | 2001-114740 | 4/2001 |
| JP | 2001-187771 | 7/2001 |
| JP | 3214975 | 7/2001 |
| JP | 2003-507180 | 2/2003 |
| JP | 2003-117397 | 4/2003 |
| JP | 3534431 | 3/2004 |
| JP | 2005-162707 | 6/2005 |
| WO | WO 97/33863 | 9/1997 |

OTHER PUBLICATIONS

U.S. Appl. No. 12/446,759, filed Apr. 23, 2009, Yanagita, et al.

*Primary Examiner* — Kamal Saeed
(74) *Attorney, Agent, or Firm* — Oblon, Spivak, McClelland, Maier & Neustadt, L.L.P.

(57) ABSTRACT

A catalyst for producing acrylonitrile capable of maintaining a high yield of acrylonitrile for a long time is provided. The catalyst has a composition represented by $Mo_aBi_bFe_cW_d Rb_eA_fB_gC_hD_iO_j(SiO_2)_k$, wherein A is Ni, Mg, Ca, Sr, Ba, Mn, Co, Cu, Zn, Cd or mixture thereof; B is Al, Cr, Ga, Y, In, La, Ce, Pr, Nd, Sm or mixture thereof; C is Ti, Zr, V, Nb, Ta, Ge, Sn, Pb, Sb, P, B, Te or mixture thereof; D is Ru, Rh, Pd, Re, Os, Ir, Pt, Ag or mixture thereof; $SiO_2$ is silica, when a is 10, b is 0.1 to 1.5, c is 0.5 to 3.0, d is 0.01 to 2.0, e is 0.02 to 1.0, f is 2.0 to 9.0, g is 0 to 5, h is 0 to 3, i is 0 to 2, k is 10 to 200; and j is the atomic ratio of oxygen determined by the valence of other elements (excluding silicon); and $(a\times2+d\times2)/(b\times3+c\times3+e\times1+f\times2+g\times3)$ is 0.90 to 1.00.

9 Claims, No Drawings

CATALYST FOR PRODUCING ACRYLONITRILE AND PROCESS FOR PRODUCING ACRYLONITRILE

Priority is claimed of Japanese Patent Application No. 2008-052272, filed Mar. 3, 2008, the content of which is incorporated herein by reference.

BACKGROUND OF THE INVENTION

1. Field of the Invention

The present invention relates to a catalyst for producing acrylonitrile by vapor phase ammoxidation of propylene by molecular oxygen and ammonia, and to a process for producing acrylonitrile using the catalyst.

2. Description of Related Art

Numerous proposals have been made regarding catalysts for producing acrylonitrile by vapor phase ammoxidation of propylene by molecular oxygen and ammonia. For example, catalysts have been disclosed having as main components thereof molybdenum, bismuth and iron, and which are further compounded with various metal components (Patent Documents 1 to 11).

In addition, methods for regenerating a catalyst by adding a molybdenum-containing substance to an inactivated molybdenum-containing catalyst, and methods for maintaining long-term performance of a catalyst by adding a molybdenum-containing substance to a molybdenum-containing catalyst, have been proposed (Patent Documents 12 to 16).

A method was found for greatly improving the selectivity of acrylonitrile by using one or more elements selected from the group consisting of potassium, rubidium and cesium as trace essential alkaline metal elements contained in catalysts used in the reactions described above, and controlling the amounts thereof within a proper range, while also inhibiting reductions in acrylonitrile yield over time by replenishing with a catalyst having a high content of alkaline metal elements since the alkaline metal elements are lost in the reaction (Patent Document 17).

In addition, in the case of adding sodium to a catalyst, the sodium was found to not only strengthen attrition resistance, but also enhance both the degree of activity and selectivity when used with a specific element (germanium) (Patent Document 18).

[Patent Document 1] U.S. Pat. No. 5,212,137
[Patent Document 2] U.S. Pat. No. 5,688,739
[Patent Document 3] U.S. Pat. No. 5,834,394
[Patent Document 4] Japanese Patent Publication No. 3214975
[Patent Document 5] Japanese Patent Publication No. 3534431
[Patent Document 6] US Patent Application No. 2004/0106817
[Patent Document 7] Japanese Unexamined Patent Application, First Publication No. H10-043595
[Patent Document 8] Japanese Laid-Open Patent Application No. 2001-114740
[Patent Document 9] Japanese Laid-Open Patent Application No. 2001-187771
[Patent Document 10] Japanese Laid-Open Patent Application No. 2003-117397
[Patent Document 11] Japanese Unexamined Patent Application, First Publication No. H8-027089
[Patent Document 12] Japanese Examined Patent Application, Second Publication No. S58-57422
[Patent Document 13] Japanese Unexamined Patent Application, First Publication No. S59-193136
[Patent Document 14] German Patent Application No. 3311521
[Patent Document 15] Japanese Examined Patent Application, Second Publication No. H2-56938
[Patent Document 16] International Publication No. WO 97/33863
[Patent Document 17] Japanese Laid-Open Patent Application No. 2005-162707
[Patent Document 18] Published Japanese translation No. 2003-507180 of PCT International Publication

SUMMARY OF THE INVENTION

However, as described in Patent Documents 1 to 16, in the case of using a molybdenum-containing catalyst as a fluidized bed catalyst of a fluidized bed reactor and further adding a molybdenum-containing substance, the molybdenum originating in the catalyst and molybdenum-containing substance vaporizes and is deposited on the cooling coil of the fluidized bed reactor. If the molybdenum is deposited on the cooling coil, there are cases in which it becomes difficult to stably operate the fluidized bed reactor for long periods of time due to heat transfer inhibition.

In addition, although selection of the type of alkaline metal element and setting of the content thereof are important elements for developing a high-performance catalyst, the acrylonitrile yield obtained with the catalyst and usage method thereof described in Patent Documents 17 and 18 were not necessarily satisfactory.

Accordingly, in order to stably produce acrylonitrile on an industrial scale, it is desirable to reduce the amount of molybdenum-containing substance added, and in order to accomplish this, it is desirable to develop a catalyst for producing acrylonitrile capable of maintaining a high acrylonitrile yield for a long period of time adding molybdenum containing substances in as small amount as possible.

An object of the present invention is to provide a catalyst for producing acrylonitrile capable of maintaining a high acrylonitrile yield for a long period of time adding molybdenum containing substances in as small amount as possible, and to provide a process for producing acrylonitrile enabling stable production of acrylonitrile on an industrial scale at a high acrylonitrile yield.

As a result of conducting extensive studies on a catalyst for producing acrylonitrile containing molybdenum, bismuth and iron, the inventors of the present invention found that by further compounding these components with specific metal components at specific ratios, a high acrylonitrile yield can be stably maintained for a long period of time even if the added amount of molybdenum-containing substance is reduced. Moreover, the inventors of the present invention also found that the selectivity of by-products (mainly carbon dioxide) can be lowered over time by selecting specific elements among specific metal components as alkaline metal elements and limiting their content to a specific range. It was also found that since the acrylonitrile selectivity improves over time as a result thereof, acrylonitrile yield can be maintained at a higher level than conventional catalysts. The present invention has been accomplished based on the above findings.

Namely, the catalyst for producing acrylonitrile of the present invention is characterized by having the composition represented by the following general formula:

$$Mo_aBi_bFe_cW_dRb_eA_fB_gC_hD_iO_j(SiO_2)_k$$

In the formula, Mo is molybdenum; Bi is bismuth; Fe is iron; W is tungsten; Rb is rubidium; O is oxygen; component A is at least one element selected from the group consisting of nickel, magnesium, calcium, strontium, barium, manganese, cobalt, copper, zinc and cadmium; component B is at least one element selected from the group consisting of aluminum, chromium, gallium, yttrium, indium, lanthanum, cerium, praseodymium, neodymium and samarium; component C is at least one element selected from the group consisting of titanium, zirconium, vanadium, niobium, tantalum, germanium, tin, lead, antimony, phosphorous, boron and tellurium; component D is at least one element selected from the group consisting of ruthenium, rhodium, palladium, rhenium, osmium, iridium, platinum and silver; $SiO_2$ is silica; a, b, c, d, e, f, g, h, i, j and k is the atomic ratio of each element (silicon in the case of silica), wherein when a=10, b is 0.1 to 1.5, c is 0.5 to 3.0, d is 0.01 to 2.0, e is 0.02 to 1.0, f is 2.0 to 9.0, g is 0 to 5, h is 0 to 3, i is 0 to 2, and k is 10 to 200, and j is the atomic ratio of oxygen required to satisfy the valence of each of the elements (excluding silicon); and $(a \times 2 + d \times 2)/(b \times 3 + c \times 3 + e \times 1 + f \times 2 + g \times 3)$ is 0.90 to 1.00.

The process for producing acrylonitrile of the present invention is characterized by producing acrylonitrile by reacting propylene, molecular oxygen and ammonia in the presence of the catalyst for producing acrylonitrile of the present invention.

According to the catalyst for producing acrylonitrile of the present invention, a high yield of acrylonitrile can be maintained for a long period of time with as small an added amount of molybdenum-containing substance as possible. In addition, since the acrylonitrile selectivity improves as a result of lowering the selectivity of by-products (mainly carbon dioxide), acrylonitrile can be stably produced at high yield and on an industrial scale over a long period of time.

DETAILED DESCRIPTION OF THE INVENTION

The catalyst for producing acrylonitrile of the present invention is a catalyst consisting of a complex oxide having a composition represented by the following general formula:

$$Mo_aBi_bFe_cW_dRb_eA_fB_gC_hD_iO_j(SiO_2)_k$$

In the formula, Mo is molybdenum; Bi is bismuth; Fe is iron; W is tungsten; Rb is rubidium; O is oxygen; component A is at least one element selected from the group consisting of nickel, magnesium, calcium, strontium, barium, manganese, cobalt, copper, zinc and cadmium; component B is at least one element selected from the group consisting of aluminum, chromium, gallium, yttrium, indium, lanthanum, cerium, praseodymium, neodymium and samarium; component C is at least one element selected from the group consisting of titanium, zirconium, vanadium, niobium, tantalum, germanium, tin, lead, antimony, phosphorous, boron and tellurium; component D is at least one element selected from the group consisting of ruthenium, rhodium, palladium, rhenium, osmium, iridium, platinum and silver; and $SiO_2$ is silica.

In addition, in the formula, a, b, c, d, e, f, g, h, i, j and k is the atomic ratio of each element (silicon in the case of silica), when a=10, b is 0.1 to 1.5, preferably 0.2 to 1.2, c is 0.5 to 3.0, preferably 0.6 to 2.5, d is 0.01 to 2.0, preferably 0.1 to 1.5, e is 0.02 to 1.0, preferably 0.05 to 0.8, f is 2.0 to 9.0, preferably 3.0 to 8.0, g is 0 to 5, preferably 0 to 3, h is 0 to 3, preferably 0 to 2, i is 0 to 2, preferably 0 to 1, and k is 10 to 200, and j is the atomic ratio of oxygen required to satisfy the valence of each of the elements (excluding silicon).

In the catalyst for producing acrylonitrile of the present invention, when a =10, X/Y as represented by the following equation is 0.90 to 1.00 and preferably 0.92 to 0.99:

$$X/Y=(a \times 2+d \times 2)/(b \times 3+c \times 3+e \times 1+f \times 2+g \times 3)$$

X is the sum of the product of the valence of molybdenum as molybdic acid (2) and the atomic ratio (a), and the product of the valence of tungsten as tungstic acid (2) and the atomic ratio (d).

Y is the sum of the product of the valence of bismuth (3) and the atomic ratio (b), the product of the valence of iron (3) and the atomic ratio (c), the product of the valence of rubidium (1) and the atomic ratio (e), the product of the valence of component A (2) and the atomic ratio (f), and the product of the valence of component B (3) and the atomic ratio (g).

Molybdenum, bismuth, iron, tungsten, rubidium, component A and silica are essential components, and the object of the present invention cannot be achieved unless each is within the composition range of the aforementioned general formula. It is particularly important in the present invention that during preparation of a catalyst contains molybdenum and tungsten as essential components thereof, metal elements capable of forming a salt with molybdic acid and tungstic acid (bismuth, iron, rubidium, component A and component B) are added in a suitable amount.

Namely, in the case the value of X/Y exceeds the upper limit thereof, since there is a shortage of the metal element serving as counter ions of the excess molybdenum exists in the catalyst molybdic acid and tungstic acid, the molybdic acid ends up being excess in the catalyst. As a result, the amount of vaporized molybdenum becomes excessively large resulting in increased deposit on the cooling coil and the like used to remove heat of the fluidized bed reactor.

On the other hand, if the value of X/Y is below the lower limit thereof, since there is an excess of the metal element serving as counter ions of the excess molybdenum exists in the catalyst and tungstic acid, the excess metal element ends up becoming an oxide and the like without forming a molybdate and tungstate. As a result, the selectivity of acrylonitrile decreases during production of acrylonitrile using the resulting catalyst.

In addition, in the catalyst for producing acrylonitrile of the present invention, the selection of rubidium among the metal components and the use of only rubidium as an alkaline metal element is an essential requirement. As a result of satisfying this requirement and limiting the content of rubidium to a specific range as previously described, the selectivity of by-products (mainly carbon dioxide) decreases over time, thereby resulting in an increase in the acrylonitrile selectivity over time and allowing the obtaining of a high yield of acrylonitrile as compared with conventional catalysts.

In the case of combining the use of other alkaline metal elements in addition to rubidium, sodium not only has a low level of selectivity, but also decreases in stability over time. Potassium is lost during the reaction, thereby adding replenishing catalysts containing large amounts of alkaline metal is required. In the case of cesium, the yield of by-products (acrolein) is high due to the high combustibility of ammonia, and the yield of hydrocyanic acid, which is an industrially important by-product, decreases.

In the present invention, the composition of the catalyst for producing acrylonitrile refers to the bulk composition of the catalyst, and provided that remarkably highly volatile components are not used, the catalyst composition (atomic ratio) may be calculated from the charged amounts of the raw materials of each element that composes the catalyst.

In the case of using the catalyst for producing acrylonitrile of the present invention in a fluidized bed, the shape thereof is preferably spherical. In addition, particle size thereof is preferably within the range of 1 to 200 μm and particularly preferably within the range of 5 to 150 μm.

The method for preparing the catalyst for producing acrylonitrile of the present invention preferably consists of preparing an aqueous slurry containing raw materials of each element that composes the catalyst, drying the resulting aqueous slurry, and calcining the resulting dried product at a temperature of 500 to 750° C.

All of elements desired to compose the catalyst are preferably contained in the aqueous slurry at the desired atomic ratios thereof. In the case all elements desired to compose the catalyst are not contained at the desired atomic ratios thereof, the resulting catalyst may be impregnated with elements not present in adequate amounts.

Examples of raw materials of each element include oxides of each element or nitrates, ammonium salts and hydroxides that can be easily converted to oxides.

Examples of raw materials of the molybdenum component include ammonium paramolybdate, ammonium dimolybdate, molybdenum trioxide, molybdenum dioxide, molybdic acid and molybdenum chloride.

Examples of raw materials of the bismuth component include bismuth oxide, bismuth nitrate, bismuth carbonate and bismuth subcarbonate.

Examples of raw materials of the iron component include iron (III) nitrate, iron (III) oxide, ferrosoferric oxide, iron (II) chloride and iron (III) chloride. In addition, metallic iron may be used after dissolving in nitric acid and the like.

Examples of raw materials of the tungsten component include ammonium paratungstate, ammonium metatungstate and tungsten trioxide.

Examples of raw materials of the rubidium component include rubidium nitrate, rubidium carbonate and rubidium hydroxide.

Examples of raw materials of other elements include nitrates, carbonates, acetates, ammonium salts, oxides, hydroxides and halides of each element.

A plurality of raw materials of each element may also be combined.

Colloidal silica is preferable for the silica raw material. The colloidal silica may be suitably selected from commercially available products. The average particle size of colloidal particles in the colloidal silica is preferably 2 to 100 nm and particularly preferably 5 to 80 nm. In addition, the colloidal silica may be that in which the particle size distribution of colloidal particles has a single peak or that in which the particle size distribution of colloidal particles is consist of multiple peaks.

For drying the aqueous slurry, a rotating disk-type spray dryer, pressure nozzle-type spray dryer or two-fluid nozzle-type spray dryer and the like are preferably used since a spherical shape is preferable for the shape of the resulting dried product and adjustment of particle diameter is comparatively easy in the case of using the catalyst in a fluidized bed.

A desirable catalyst active structure is formed by calcining the resulting dried product at a temperature within the range of 500 to 750° C. Since a satisfactory catalyst is not obtained if the calcining time is too short, the calcining time is preferably 1 hour or more, and since extraordinary effects are not obtained even if calcining time is extended beyond the required calcining time, the calcining time is normally 20 hours or less. A method using a general-purpose calcining furnace can be used for the calcining method without any particular limitations. The calcining furnace is preferably a rotary kiln or fluidized bed calciner and the like.

During calcining, although the dried product may be immediately calcining at a temperature within the range of 500 to 750° C., calcining is more preferably carried out by preliminarily calcining in one to two stages at a temperature of 250 to 400° C. and/or 400 to 490° C. followed by calcining at a temperature within the range of 500 to 750° C.

When producing acrylonitrile by vapor phase ammoxidation of propylene by molecular oxygen (to simply be referred to as oxygen) and ammonia using the catalyst for producing acrylonitrile of the present invention, air is industrially advantageous as the oxygen source. Oxygen-enriched air may also be used by adding pure oxygen as necessary.

In addition, a fluidized bed reactor is preferably used for the reactor, and a fluidized bed reactor equipped with a cooling means such as a cooling coil, cooling pipe or heat exchanger and the like may also be used.

The concentration of propylene in the raw material gas can be varied over a wide range, is suitably 1 to 20% by volume and particularly preferably 3 to 15% by volume.

The molar ratio of propylene to oxygen in the raw material gas (propylene:oxygen) is preferably 1:1.5 to 1:3. In addition, the molar ratio of propylene to ammonia in the reaction gas (propylene:ammonia) is preferably 1:1 to 1:1.5.

The raw material gas may be diluted with an inert gas or water vapor and the like.

The reaction pressure when carrying out vapor phase ammoxidation is preferably from atmospheric pressure to 500 kPa.

The reaction temperature when carrying out vapor phase ammoxidation is preferably within the range of 400 to 500° C.

In this manner, according to the catalyst for producing acrylonitrile of the present invention, since the amount of molybdenum vaporized from the catalyst can be reduced, the added amount of molybdenum-containing substance can also be reduced. Moreover, by selecting rubidium from specific metal components and using as an alkaline metal component, and further limiting the content of rubidium to a specific range as previously described, the selectivity of by-products (mainly carbon dioxide) can be lowered, thereby improving the selectivity of acrylonitrile over time, and making it possible to stably maintain a high yield of acrylonitrile as compared with conventional catalysts.

EXAMPLES

Effects of the present invention are indicated through the following examples. The term "parts" in the following examples and comparative examples refers to parts by mass.

Activity tests of catalysts were carried out according to the procedure described below.

(1) Activity Tests of Catalysts:

Production of acrylonitrile by ammoxidation of propylene was carried out using a fluidized bed reactor having an inner diameter of 43 mm and length of 1 m.

At that time, a mixed gas of propylene, ammonia, air and water vapor at a molar ratio of 1/1.2/9.5/0.5 was introduced into the reactor at a gas linear velocity of 8 cm/sec, the reaction temperature was set to 430° C. and the reaction pressure was set to 200 kPa. In addition, an analysis of the reactive test was carried out at a frequency of one or more times per 100 hours, and the amount of catalyst was suitably adjusted so that the propylene conversion was 98.0 to 98.2%.

Furthermore, during production of acrylonitrile, 0.02% by mass of molybdenum based on the mass of the catalyst was added at the rate of once a week in the form of ammonium paramolybdate.

The analyses of the reactive test were carried out by gas chromatography.

In addition, propylene conversion, acrylonitrile selectivity, acrylonitrile yield and carbon dioxide yield were defined in the manner indicated below.

Propylene conversion (%)=$Q/P \times 100$
Acrylonitrile selectivity (%)=$R/Q \times 100$
Acrylonitrile yield (%)=$R/P \times 100$
Carbon dioxide yield (%)=$S/P \times 100$ Here, P represents the number of moles of propylene supplied to the reaction, Q represents the number of moles of propylene that reacted, R represents the number of moles of acrylonitrile formed, and S represents the number of moles of carbon dioxide formed.

Example 1

A solution of 1958.2 parts of ammonium paramolybdate dissolved in 4000 parts of water was added to 11662.2 parts of 20% by mass silica sol while stirring followed by heating to 40° C. (Liquid A).

Separate from the above, 322.8 parts of bismuth nitrate were dissolved in 1600 parts of 17% by mass nitric acid while stirring followed by the sequential addition of 672.1 parts of iron (III) nitrate, 1451.4 parts of nickel nitrate, 284.4 parts of magnesium nitrate, 289.0 parts of cerium nitrate, 161.4 parts of cobalt nitrate, 212.4 parts of yttrium nitrate and 13.2 parts of rubidium nitrate to this solution followed by heating to 45° C. (Liquid B).

After adding Liquid B to Liquid A while stirring, 289.6 parts of a 50% aqueous solution of ammonium metatungstate (50% by mass as $WO_3$) heated to 45° C. were added thereto to obtain a slurry.

The resulting slurry was dried with a rotating disk-type spray dryer while controlling the temperature at the hot air inlet to 280° C. and the temperature at the outlet to 150° C.

After preliminarily calcining the dried product for 2 hours at 300° C. and then for 2 hours at 450° C., the slurry was calcined in a fluidized bed calciner for 3 hours at 600° C. to obtain a catalyst.

The composition of the catalyst obtained in this manner was calculated from the charged amounts of the raw materials as indicated below.

$$Mo_{10}Bi_{0.6}Fe_{1.5}W_{0.5}Rb_{0.15}Ni_{4.5}Mg_1Co_{0.5}Y_{0.5}Ce_{0.6}O_x (SiO_2)_{35}$$

Here, x represents the atomic ratio of oxygen required to satisfy the valence of each of the other elements (excluding silicon).

When the resulting catalyst was tested for activity under the conditions indicated in (1) above, the acrylonitrile yield progressed favorably, demonstrating a value of 81.6% 50 hours after the start of the reaction, 82.3% 500 hours after the start of the reaction and 82.5% 1000 hours after the start of the reaction. The results are shown in Table 3.

Example 2

A catalyst having the composition shown in Table 1 was prepared in the same manner as Example 1.

Namely, Liquid A was prepared using the same method as Example 1, Liquid B was prepared using the same method as Example 1 with the exception of adding gallium nitrate and rhenium nitrate in that order instead of yttrium nitrate, and a catalyst was prepared in the same manner as Example 1 with the exception of changing the calcining conditions to the conditions shown in Table 3 followed by testing catalyst activity under the conditions indicated in (1) above. The results are shown in Table 3.

Example 3

A catalyst having the composition shown in Table 1 was prepared in the same manner as Example 1.

Namely, Liquid A was prepared using the same method as Example 1, Liquid B was prepared using the same method as Example 1 with the exception of adding manganese nitrate, lanthanum nitrate and phosphoric acid in that order instead of yttrium nitrate, and a catalyst was prepared in the same manner as Example 1 with the exception of changing the calcining conditions to the conditions shown in Table 3 followed by testing catalyst activity under the conditions indicated in (1) above. The results are shown in Table 3.

Example 4

A catalyst having the composition shown in Table 1 was prepared in the same manner as Example 1.

Namely, Liquid A was prepared using the same method as Example 1, Liquid B was prepared using the same method as Example 1 with the exception of adding strontium nitrate instead of cobalt nitrate and adding neodymium nitrate, niobium oxide and vanadium nitrate in that order instead of yttrium nitrate, and a catalyst was prepared in the same manner as Example 1 with the exception of changing the calcining conditions to the conditions shown in Table 3 followed by testing catalyst activity under the conditions indicated in (1) above. The results are shown in Table 3.

Example 5

A catalyst having the composition shown in Table 1 was prepared in the same manner as Example 1.

Namely, Liquid A was prepared using the same method as Example 1, Liquid B was prepared using the same method as Example 1 with the exception of adding zinc nitrate instead of magnesium nitrate, adding niobium oxide instead of yttrium nitrate, and adding iridium oxide instead of cerium nitrate, and a catalyst was prepared in the same manner as Example 1 with the exception of changing the calcining conditions to the conditions shown in Table 3 followed by testing catalyst activity under the conditions indicated in (1) above. The results are shown in Table 3.

Example 6

A catalyst having the composition shown in Table 1 was prepared in the same manner as Example 1.

Namely, Liquid A was prepared using the same method as Example 1, Liquid B was prepared using the same method as Example 1 with the exception of zinc nitrate instead of magnesium nitrate, adding lanthanum nitrate instead of cobalt nitrate, adding samarium nitrate instead of yttrium nitrate, adding telluric acid instead of cerium nitrate and adding phosphoric acid in that order, and a catalyst was prepared in the same manner as Example 1 with the exception of changing the calcining conditions to the conditions shown in Table 3 followed by testing catalyst activity under the conditions indicated in (1) above. The results are shown in Table 3.

Example 7

A catalyst having the composition shown in Table 1 was prepared in the same manner as Example 1.

Namely, Liquid A was prepared using the same method as Example 1, Liquid B was prepared using the same method as Example 1 with the exception of adding chromium nitrate instead of yttrium nitrate, and a catalyst was prepared in the same manner as Example 1 with the exception of changing the calcining conditions to the conditions shown in Table 3 followed by testing catalyst activity under the conditions indicated in (1) above. The results are shown in Table 3.

Example 8

A catalyst having the composition shown in Table 1 was prepared in the same manner as Example 1.

Namely, Liquid A was prepared using the same method as Example 1, Liquid B was prepared using the same method as Example 1 with the exception of adding manganese nitrate instead of cobalt nitrate and zinc nitrate in that order, praseodymium nitrate instead of yttrium nitrate, phosphoric acid and germanium nitrate in that order, and a catalyst was prepared in the same manner as Example 1 with the exception of changing the calcining conditions to the conditions shown in Table 3 followed by testing catalyst activity under the conditions indicated in (1) above. The results are shown in Table 3.

Example 9

A catalyst having the composition shown in Table 1 was prepared in the same manner as Example 1.

Namely, Liquid A was prepared using the same method as Example 1, Liquid B was prepared using the same method as Example 1 with the exception of adding chromium nitrate instead of cobalt nitrate, lanthanum nitrate instead of yttrium nitrate, lead nitrate instead of cerium nitrate, phosphoric acid and boric acid in that order, and a catalyst was prepared in the same manner as Example 1 with the exception of changing the calcining conditions to the conditions shown in Table 3 followed by testing catalyst activity under the conditions indicated in (1) above. The results are shown in Table 3.

Comparative Example 1

A catalyst having the composition shown in Table 2 was prepared in the same manner as Example 1.

Namely, Liquid A was prepared using the same method as Example 1, Liquid B was prepared using the same method as Example 1 with the exception of adding sodium nitrate instead of rubidium nitrate, and a catalyst was prepared in the same manner as Example 1 under the calcining conditions shown in Table 3 followed by testing catalyst activity under the conditions indicated in (1) above. The results are shown in Table 3.

Comparative Example 2

A catalyst having the composition shown in Table 2 was prepared in the same manner as Example 1.

Namely, Liquid A was prepared using the same method as Example 1, Liquid B was prepared using the same method as Example 1 with the exception of adding potassium nitrate following addition of rubidium nitrate, and a catalyst was prepared in the same manner as Example 1 under the calcining conditions shown in Table 3 followed by testing catalyst activity under the conditions indicated in (1) above. The results are shown in Table 3.

Comparative Example 3 and 4

Catalysts having the compositions shown in Table 2 were prepared in the same manner as Example 1.

Namely, Liquid B was prepared using the same method as Example 1, Liquid A was prepared using the same method as Example 1 with the exception of changing the added amount of molybdenum so as to obtain catalyst different X/Y values, and catalysts were prepared in the same manner as Example 1 under the calcining conditions shown in Table 3 followed by testing catalyst activity under the conditions indicated in (1) above. The results are shown in Table 3.

TABLE 1

| | | Mo | Bi | Fe | W | Rb | A | | | | B | | | C | | | D | | Si | X/Y |
|---|---|---|---|---|---|---|---|---|---|---|---|---|---|---|---|---|---|---|---|---|
| EXAMPLES | 1 | 10 | 0.6 | 1.5 | 0.5 | 0.15 | Ni | Mg | Co | | Y | Ce | | | | | | | 35 | 0.97 |
| | | | | | | | 4.5 | 1 | 0.5 | | 0.5 | 0.6 | | | | | | | | |
| | 2 | 10 | 0.6 | 1.5 | 0.8 | 0.15 | Ni | | | | Ga | Ce | | | | | Re | | 50 | 0.93 |
| | | | | | | | 6.5 | | | | 0.7 | 0.6 | | | | | 0.01 | | | |
| | 3 | 10 | 0.5 | 1.3 | 0.5 | 0.15 | Ni | Mg | Mn | Co | Ce | La | | P | | | | | 35 | 0.98 |
| | | | | | | | 4.5 | 1 | 0.2 | 1.3 | 0.3 | 0.3 | | 0.2 | | | | | | |
| | 4 | 10 | 1.0 | 1.5 | 0.8 | 0.08 | Ni | Mg | Sr | | Nd | | | Nb | V | | | | 35 | 0.94 |
| | | | | | | | 0.5 | 3.5 | 1.5 | | 1.5 | | | 0.2 | 0.2 | | | | | |
| | 5 | 10 | 0.8 | 1.0 | 0.05 | 0.12 | Ni | Co | Zn | | | | | Nb | | | Ir | | 35 | 0.92 |
| | | | | | | | 1.2 | 5 | 2 | | | | | 0.1 | | | 0.1 | | | |
| | 6 | 10 | 0.5 | 2.2 | 0.5 | 0.10 | Ni | Zn | | | La | Sm | Te | P | | | | | 45 | 0.96 |
| | | | | | | | 3.5 | 1.5 | | | 1 | 0.2 | 0.2 | 0.1 | | | | | | |
| | 7 | 10 | 0.6 | 1.8 | 1.2 | 0.30 | Ni | Mg | Co | | Ce | Cr | | | | | | | 35 | 0.98 |
| | | | | | | | 4.5 | 1 | 0.5 | | 0.6 | 0.5 | | | | | | | | |
| | 8 | 10 | 0.4 | 1.2 | 0.4 | 0.13 | Ni | Mg | Mn | Zn | Ce | Pr | | P | | Ge | | | 40 | 0.97 |
| | | | | | | | 6 | 1 | 0.1 | 0.1 | 0.6 | 0.1 | | 0.05 | | 0.01 | | | | |
| | 9 | 10 | 0.8 | 1.5 | 0.2 | 0.20 | Ni | Mg | | | Cr | La | Pb | P | B | | | | 30 | 0.93 |
| | | | | | | | 0.5 | 3 | | | 2 | 0.6 | 0.01 | 0.1 | 0.1 | | | | | |

TABLE 2

| | | Mo | Bi | Fe | W | Rb | A | | | B | | C | D | Alkaline metal (excl. Rb) | Si | X/Y |
|---|---|---|---|---|---|---|---|---|---|---|---|---|---|---|---|---|
| Comparative Examples | 1 | 10 | 0.6 | 1.5 | 0.5 | | Ni 4.5 | Mg 1 | Co 0.5 | Y 0.5 | Ce 0.6 | | | Na 0.15 | 35 | 0.97 |
| | 2 | 10 | 0.6 | 1.5 | 0.5 | 0.15 | Ni 4.5 | Mg 1 | Co 0.5 | Y 0.5 | Ce 0.6 | | | K 0.04 | 35 | 0.97 |
| | 3 | 9 | 0.6 | 1.5 | 0.5 | 0.15 | Ni 4.5 | Mg 1 | Co 0.5 | Y 0.5 | Ce 0.6 | | | | 35 | 0.87 |
| | 4 | 11 | 0.6 | 1.5 | 0.5 | 0.15 | Ni 4.5 | Mg 1 | Co 0.5 | Y 0.5 | Ce 0.6 | | | | 35 | 1.06 |

TABLE 3

| | | Calcining Conditions | | Reaction Conditions | Acrylonitrile Yield (%) | | | Carbon Dioxide Yield (%) | | |
|---|---|---|---|---|---|---|---|---|---|---|
| | | Temp. (°C.) | Time (hr) | Temp. (°C.) | Elapsed time (hr) | | | Elapsed time (hr) | | |
| | | | | | 50 | 500 | 1000 | 50 | 500 | 1000 |
| Examples | 1 | 600 | 3 | 430 | 81.6 | 82.3 | 82.5 | 6.8 | 6.2 | 5.9 |
| | 2 | 640 | 3 | 430 | 81.9 | 82.6 | 82.7 | 6.6 | 6.3 | 6.2 |
| | 3 | 590 | 3 | 430 | 81.4 | 82.1 | 82.2 | 6.8 | 6.3 | 6.0 |
| | 4 | 640 | 3 | 430 | 80.5 | 81.2 | 82.0 | 7.1 | 6.5 | 6.2 |
| | 5 | 620 | 3 | 430 | 81.0 | 81.4 | 81.5 | 6.8 | 6.4 | 6.3 |
| | 6 | 610 | 3 | 430 | 82.0 | 82.2 | 82.5 | 6.6 | 6.2 | 5.8 |
| | 7 | 530 | 3 | 430 | 81.7 | 81.9 | 82.1 | 6.8 | 6.2 | 6.0 |
| | 8 | 580 | 3 | 430 | 81.5 | 82.2 | 82.4 | 7.0 | 6.4 | 6.0 |
| | 9 | 580 | 3 | 430 | 81.2 | 82.0 | 82.2 | 6.7 | 6.2 | 5.8 |
| Comparative Examples | 1 | 600 | 3 | 430 | 80.3 | 79.6 | 79.3 | 7.5 | 7.6 | 7.7 |
| | 2 | 600 | 3 | 430 | 78.5 | 78.3 | 77.9 | 7.2 | 7.0 | 7.0 |
| | 3 | 600 | 3 | 430 | 79.0 | 78.5 | 78.3 | 7.0 | 6.8 | 6.9 |
| | 4 | 600 | 3 | 430 | 80.1 | 79.5 | 79.3 | 7.6 | 7.6 | 7.5 |

As is clear from Table 3, in the case of using catalysts for producing acrylonitrile obtained in each of the examples, the acrylonitrile yield progressed favorably at 50 hours, 500 hours and 1000 hours after the start of the reaction. In addition, the yield of by-product in the form of carbon dioxide decreased over time.

On the other hand, in the case of using catalysts for producing acrylonitrile obtained in each of the comparative examples, the acrylonitrile yield decreased with time at 50 hours, 500 hours and 1000 hours after the start of the reaction. In addition, it was more difficult to achieve decreases in carbon dioxide yield as compared with the examples.

According to the catalyst for producing acrylonitrile of the present invention, since amount of molybdenum vaporized from the catalyst can be reduced when producing acrylonitrile by vapor phase ammoxidation of propylene, the amount of molybdenum-containing substance added can be reduced. Moreover, as a result of a time-based decrease in the selectivity of by-products (mainly carbon dioxide), the selectivity of acrylonitrile increases over time, thereby making it possible to a high acrylonitrile yield as compared with conventional catalysts.

Namely, use of the catalyst for producing acrylonitrile of the present invention enables long-term continuous operation while significantly reducing being deposited of molybdenum on cooling coils, while also making it possible to maintain a higher acrylonitrile yield as compared with conventional catalysts, thereby allowing the catalyst for producing acrylonitrile of the present invention to have considerable industrial value.

What is claimed is:

1. A catalyst for having a composition represented by formula (1):

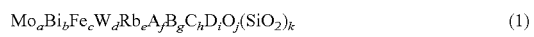

$$Mo_a Bi_b Fe_c W_d Rb_e A_f B_g C_h D_i O_j (SiO_2)_k \qquad (1)$$

wherein

A is at least one element selected from the group consisting of nickel, magnesium, calcium, strontium, barium, manganese, cobalt, copper, zinc, and cadmium;

B is at least one element selected from the group consisting of aluminum, chromium, gallium, yttrium, indium, lanthanum, cerium, praseodymium, neodymium, and samarium;

C is at least one element selected from the group consisting of titanium, zirconium, vanadium, niobium, tantalum, germanium, tin, lead, antimony, phosphorous, boron, and tellurium;

D is at least one element selected from the group consisting of ruthenium, rhodium, palladium, rhenium, osmium, iridium, platinum, and silver;

$SiO_2$ is silica;

a, b, c, d, e, f, g, h, i, j and k are atomic ratios of each element, or silicon in the case of silica, wherein, when a=10, b is 0.1 to 1.5, c is 0.5 to 3.0, d is 0.01 to 2.0, e is 0.02 to 1.0, f is 2.0 to 9.0, g is 0 to 5, h is 0 to 3, i is 0 to 2, and k is 10 to 200, and j is the atomic ratio of oxygen required to satisfy the valence of each of the elements, excluding silicon; and $(a \times 2 + d \times 2)/(b \times 3 + c \times 3 + e \times 1 + f \times 2 + g \times 3)$ is 0.90 to 1.00.

2. The catalyst of claim 1, wherein, when a =10:
b is 0.2 to 1.2; and
j is the atomic ratio of oxygen required to satisfy the valence of each of the elements, excluding silicon.

3. The catalyst of claim 1, wherein, when a =10:
c is 0.6 to 2.5; and
j is the atomic ratio of oxygen required to satisfy the valence of each of the elements, excluding silicon.

4. The catalyst of claim 1, wherein, when a =10:
d is 0.1 to 1.5; and
j is the atomic ratio of oxygen required to satisfy the valence of each of the elements, excluding silicon.

5. The catalyst of claim 1, wherein, when a =10:
e is 0.05 to 0.8; and
j is the atomic ratio of oxygen required to satisfy the valence of each of the elements, excluding silicon.

6. The catalyst of claim 1, wherein, when a =10:
f is 3.0 to 8.0; and
j is the atomic ratio of oxygen required to satisfy the valence of each of the elements, excluding silicon.

7. The catalyst of claim 1, having a particle size of 1 to 200 μm.

8. The catalyst of claim 1, having a particle size of 5 to 150 μm.

9. The catalyst of claim 1, wherein, when a =10:
$(a \times 2 + d \times 2)/(b \times 3 + c \times 3 + e \times 1 + f \times 2 + g \times 3)$ is 0.92 to 0.99.

* * * * *